(12) United States Patent
Klapötke et al.

(10) Patent No.: US 9,278,984 B2
(45) Date of Patent: Mar. 8, 2016

(54) METHOD FOR PREPARATION OF A LEAD-FREE PRIMARY EXPLOSIVE

(71) Applicants: PACIFIC SCIENTIFIC ENERGETIC MATERIALS COMPANY, Chandler, AZ (US); Thomas Matthias Klapötke, Munich (DE); Davin Glenn Piercey, Munich (DE)

(72) Inventors: Thomas Matthias Klapötke, Munich (DE); Davin Glenn Piercey, Munich (DE); John W. Fronabarger, Sun Lakes, AZ (US); Michael D. Williams, Gilbert, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 316 days.

(21) Appl. No.: 13/957,469

(22) Filed: Aug. 2, 2013

(65) Prior Publication Data
US 2015/0239910 A1 Aug. 27, 2015

Related U.S. Application Data

(60) Provisional application No. 61/680,766, filed on Aug. 8, 2012.

(51) Int. Cl.
*C07F 1/08* (2006.01)

(52) U.S. Cl.
CPC ........................................ *C07F 1/08* (2013.01)

(58) Field of Classification Search
CPC ......................................................... C07F 1/08
See application file for complete search history.

(56) References Cited

U.S. PATENT DOCUMENTS

| | | | |
|---|---|---|---|
| 2,066,954 A | 1/1937 | Von | |
| 2,480,141 A | 8/1949 | King | |
| 3,150,020 A | 9/1964 | Kilmer | |
| 3,351,015 A | 11/1967 | Wallack et al. | |
| 3,366,055 A | 1/1968 | Hollander | |
| 3,486,453 A | 12/1969 | Billy | |
| 3,634,510 A | 1/1972 | Louis | |
| 3,791,301 A | 2/1974 | La Costa | |
| 4,093,623 A | 6/1978 | Gilligan et al. | |
| 4,094,879 A | 6/1978 | Bates et al. | |
| 4,133,707 A | 1/1979 | Andrew | |
| 5,039,812 A | 8/1991 | Norris | |
| 5,416,535 A | 5/1995 | Sato et al. | |
| 5,417,160 A | 5/1995 | Mei et al. | |
| 5,610,367 A | 3/1997 | Erickson et al. | |
| 5,639,986 A | 6/1997 | Evans | |
| 5,717,159 A | 2/1998 | Dixon et al. | |
| 5,831,208 A | 11/1998 | Erickdon | |
| 6,478,903 B1 | 11/2002 | John et al. | |
| 7,056,401 B2 | 6/2006 | Galluzzi | |
| 7,833,330 B2 * | 11/2010 | Fronabarger et al. | 106/1.13 |
| 8,062,443 B2 | 11/2011 | Fronabarger et al. | |
| 8,071,784 B2 | 12/2011 | Fronabarger et al. | |
| 8,163,786 B2 | 4/2012 | Fronabarger et al. | |
| 8,216,401 B1 | 7/2012 | Fronabarger et al. | |
| 8,298,324 B2 * | 10/2012 | Fronabarger et al. | 106/1.13 |
| 8,440,008 B2 * | 5/2013 | Fronabarger et al. | 106/1.13 |
| 8,523,989 B2 | 9/2013 | Fronabarger et al. | |
| 2002/0143189 A1 | 10/2002 | Sonti | |
| 2005/0183805 A1 | 8/2005 | Pile et al. | |
| 2006/0030715 A1 | 2/2006 | Hiskey et al. | |
| 2007/0161801 A1 | 7/2007 | Renz et al. | |
| 2009/0069566 A1 | 3/2009 | Fronabarger et al. | |
| 2009/0223401 A1 | 9/2009 | Fronabarger et al. | |
| 2010/0280254 A1 | 11/2010 | Fronabarger et al. | |
| 2011/0108172 A1 | 5/2011 | Fronabarger et al. | |
| 2012/0024178 A1 | 2/2012 | Fronabarger et al. | |
| 2012/0077983 A1 | 3/2012 | Fronabarger et al. | |
| 2012/0152140 A1 | 6/2012 | Fronabarger et al. | |
| 2012/0215004 A1 | 8/2012 | Fronabarger et al. | |
| 2013/0204005 A1 | 8/2013 | Fronabarger et al. | |

FOREIGN PATENT DOCUMENTS

| | | | | |
|---|---|---|---|---|
| AU | 2007313468 | | 4/2008 | |
| DE | 1088855 B | | 9/1960 | |
| EP | 0596684 | | 5/1994 | |
| EP | 0941180 | | 9/1999 | |
| EP | 2018393 | | 6/2012 | |
| GB | 1106277 | | 3/1968 | |
| JP | H06316544 | | 11/1994 | |
| JP | H08504758 | | 5/1996 | |
| JP | 2006115444 | | 4/2006 | |
| WO | 9408925 | | 4/1994 | |
| WO | 9711926 | | 4/1997 | |
| WO | 9902470 | | 1/1999 | |
| WO | 9944968 | | 9/1999 | |
| WO | 2008048351 | | 4/2008 | |
| WO | WO 2008/048351 | * | 4/2008 | ............... C07F 1/08 |
| WO | 2008104000 | | 8/2008 | |
| WO | 2009114347 | | 9/2009 | |
| WO | 2010085583 | | 7/2010 | |

OTHER PUBLICATIONS

Qualification and Final (Type) Qualification Procedures for Navy Explosives, Naval Sea Systems Command Instruction #8020.5C ("NAVSEAINST 8020.5C"), 40 pages (May 5, 2000), 40 pages.
Fourth Report on the Investigation of the Alternatives to Lead Azide and Lead Styphnate, NSWC-IH contract #N00174-06-C-0079, Sep. 20, 2007, pp. 1-23.
Notice of Allowance dated Apr. 5, 2010 in U.S. Appl. No. 11/676,846.
Notice of Allowance dated Jul. 27, 2010 in U.S. Appl. No. 11/676,846.
Office Action dated Jan. 5, 2010 in U.S. Appl. No. 11/676,846.
Office Action dated Apr. 2, 2009 in U.S. Appl. No. 11/676,846.
Office Action dated Jun. 2, 2009 in U.S. Appl. No. 11/676,846.

(Continued)

*Primary Examiner* — Joseph Kosack
(74) *Attorney, Agent, or Firm* — Kilpatrick Townsend & Stockton LLP; Dean W. Russell, Esq.; Tiffany L. Williams, Esq.

(57) ABSTRACT

Described are methods for preparing copper(I) 5-nitrotetrazolate, which include reacting copper(II) sulfate pentahydrate, sodium nitrite, 5-aminotetrazole, and at least one of nitric acid and urea in water.

19 Claims, No Drawings

(56) References Cited

OTHER PUBLICATIONS

Request for Continued Examination dated Jul. 2, 2010 in U.S. Appl. No. 11/676,846.
Response dated Mar. 8, 2010 in U.S. Appl. No. 11/676,846.
Response dated Apr. 20, 2009 in U.S. Appl. No. 11/676,846.
Response dated Sep. 2, 2009 in U.S. Appl. No. 11/676,846.
Notice of Allowance dated Feb. 8, 2012 in U.S. Appl. No. 12/691,849.
Office Action dated Jul. 19, 2011 in U.S. Appl. No. 12/691,849.
Office Action dated Sep. 20, 2011 in U.S. Appl. No. 12/691,849.
Response dated Aug. 19, 2011 in U.S. Appl. No. 12/691,849.
Response dated Dec. 16, 2011 in U.S. Appl. No. 12/691,849.
Notice of Allowance dated Jul. 29, 2011 in U.S. Appl. No. 12/900,531.
Office Action dated Mar. 10, 2011 in U.S. Appl. No. 12/900,531.
Response dated Jun. 10, 2011 in U.S. Appl. No. 12/900,531.
Office Action dated Dec. 21, 2012 in U.S. Appl. No. 13/194,147.
Office Action dated Feb. 27, 2013 in U.S. Appl. No. 13/194,147.
Response dated Jan. 16, 2013 in U.S. Appl. No. 13/194,147.
Notice of Allowance dated Mar. 21, 2012 in U.S. Appl. No. 13/267,009.
Notice of Allowance dated Jun. 28, 2012 in U.S. Appl. No. 13/282,547.
Office Action dated Feb. 14, 2012 in U.S. Appl. No. 13/282,547.
Response dated May 10, 2012 in U.S. Appl. No. 13/282,547.
Notice of Allowance dated Feb. 25, 2013 in U.S. Appl. No. 13/419,455.
Office Action dated Oct. 17, 2012 in U.S. Appl. No. 13/419,455.
Response dated Jan. 17, 2013 in U.S. Appl. No. 13/419,455.
English Translation of Office Action dated Feb. 28, 2012 in Japanese Patent Application No. 2009-510942.
Office Action dated Jul. 23, 2010 in Australian Patent Application No. AU2007313468.
Response dated Jun. 20, 2011 in Australian Patent Application No. AU2007313468.
Barsan & Miller, "Health Hazard Evaluation Report", HETA Report #91-0346-2572, FBI Academy, Quantico, Virginia, Apr. 1996, pp. ii-iv & 1-33.
Office Action dated Jul. 28, 2010 in European Patent Application No. EP07861248.8.
Response dated Oct. 5, 2010 in European Patent Application No. EP07861248.8.
Office Acton dated Oct. 8, 2012 in European Patent Application No. EP10701427.6.
Fronabarger et al., "Preparation characterization and output testing of salts of 7-hydroxy-4,6-dinitrobenzofuroxan", Safe Journal Spring 2007 Survival and Flight Equipment Association (Safe) US, XP008110604, Apr. 2007, vol. 35, No. 1, pp. 14-18.
Hastie et al., Molecular Basis for Secondary Flash Suppression, U.S. Army Research Office, Jul. 1, 1986, Document ARO 18375-CH, MIPR 102-84, 26 pages.
Patani et al., "Bioisosterism: A Rational Approach in Drug Design", Chem. Rev., 1996, 96(8):3147-3176.
International Search Report and Written Opinion dated May 5, 2008 in Serial No. PCT/US07/04846.
International Search Report and Written Opinion dated Sep. 2, 2009 in Serial No. PCT/US2009/035952.
International Preliminary Examination Report dated Aug. 4, 2011 in Serial No. PCT/US2010/021695.
International Search Report and Written Opinion dated Apr. 12, 2010 in Serial No. PCT/US20101021695.
Spear et al., "Structure and Properties of the Potassium Hydroxide-Dinitrobenzofuro Xan Adduct (KDNBF) and Related Explosive Salts", Propellants, Explosive, Pyrotechnics, No. XP008110603, Jun. 3, 1983, 8:85-88.
Talawar et al., "Energetic co-ordination compounds : synthesis, characterization and thermolysis studies on bis-(5-nitro-2H-tetrazolato-N<2» tetraammine cobalt(III) perchlorate (BNCP) and itsnew transition metal (Ni/Cu/Zn) perchlorate analogues", Journal of Hazardous Materials, Elsevier Amsterdam, NL, XP022384449, ISSN : 0304-3894, Apr. 5, 2005, vol. 120, No. 1-3, pp. 25-35 (especially p. 26).
Office Action dated Jan. 2, 2013 in U.S. Appl. No. 13/612,901.
Response dated Apr. 1, 2013 in U.S. Appl. No. 13/612,901.
Notice of Allowance dated May 8, 2013 in U.S. Appl. No. 13/612,901.
English Translation of Notice of Reasons for Rejection dated Jul. 30, 2013 in Japanese Application No. 2011-548109.
English Translation of Notice of Decision of Refusal dated Jun. 24, 2014 in Japanese Application No. 2011-548109.
Chemisches Zentralblatt, Nr. 13, p. 4573, 1961 (5 pages).

* cited by examiner

METHOD FOR PREPARATION OF A LEAD-FREE PRIMARY EXPLOSIVE

CROSS-REFERENCE TO RELATED APPLICATIONS

This application claims the benefit of U.S. Provisional Patent Application Ser. No. 61/680,766, entitled "Method for Preparation of a Lead-Free Primary Explosive," filed Aug. 8, 2012, the entire contents of which is incorporated herein by this reference.

FIELD OF THE INVENTION

This invention relates to explosives, and in particular to a method for preparation of copper(I) 5-nitrotetrazolate "DBX-1", a lead-free primary explosive under consideration as a replacement for lead azide.

BACKGROUND

The design of new, environmentally friendly, primary explosives to replace lead azide has been a major topic in the research of energetic materials for many years. The unacceptable toxicity of lead azide and its detonation products mandates replacement for both ecological and personal health reasons.

However, finding a suitable replacement for lead azide is complicated by the fact that very few materials have properties which make them useful as primary explosives: the combination of a material that will undergo a deflagration to detonation transition upon ignition, while still being relatively safe to handle is quite rare in chemistry, with relatively few initiatory primary explosives known.

Recently, only one compound has been shown to be a "drop in" replacement for lead azide; requiring no redesign of initiatory devices (detonators or blasting caps) with simple replacement of lead azide by the new material. This new material was created by Pacific Scientific Energetic Materials Company ("PSEMC") and is copper(I) nitrotetrazolate or "DBX-1". DBX-1 is described in U.S. Pat. No. 7,833,330 ("the '330 patent"); U.S. Pat. No. 8,071,784 ("the '784 patent"); and U.S. Pat. No. 8,163,786 ("the '786 patent") and U.S. Publication Nos. 2012-0024178 ("the '178 publication") and 2012-0077983 ("the '983 publication"), all of which are currently assigned to PSEMC. The '330, '784, and '786 patents and the '178 and '983 publications are hereby incorporated in their entireties herein by this reference. All the explosive requirements of DBX-1 are comparable to that of RD1333 grade lead azide in that it is of comparable sensitivity and as such, safety, and also of comparable initiating performance allowing for a material that possesses all the characteristics of lead azide without the associated toxicity.

The current synthesis of DBX-1 involves preparation and isolation of sodium 5-nitrotetrazolate, which is not commercially available, from 5-aminotetrazole followed by a second reaction step which reacts sodium 5-nitrotetrazolate directly with Cu(I) (U.S. Pat. No. 8,071,784) or with Cu(II) and an in-situ reductant (U.S. Pat. No. 8,163,786) to produce copper (I) 5-nitrotetrazolate.

There is a need to improve the efficiency of the chemical process by providing a method for preparation of DBX-1 directly from 5-aminotetrazole via a single reactor process which may eliminate the step of isolating the sodium 5-nitrotetrazolate intermediate, a potentially explosive intermediate step. The process delineated in this invention provides a method for converting commercially available 5-aminotetrazole directly to DBX-1 via a single reactor process.

A further advantage of this method is the efficiency in terms of copper. A reaction, commonly known in the industry as the Sandmeyer reaction and used to produce a 5-nitrotetrazolate, utilizes copper(II) to enhance substitution of the reactive diazonium intermediate. This copper is removed and discarded as copper oxide during isolation of the sodium 5-nitrotetrazolate. Additional copper(II) is then used to convert the sodium 5-nitrotetrazolate to DBX-1. The process employed in this invention utilizes the copper(II) associated with the Sandmeyer reaction as a reactant for the formation of DBX-1.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent and claims.

According to certain embodiments of the present invention, a single reactor process for the synthesis of DBX-1 starts from 5-aminotetrazole and converts it, via a Sandmeyer reaction, to the acid copper(II) salt of 5-nitrotetrazolate. Excess nitrite is then destroyed with nitric acid, nitric acid/ascorbate, or urea and the solution is heated. An aqueous solution of sodium ascorbate is then added and the copper(I) nitrotetrazolate is precipitated from solution in the form of a precipitate.

The reaction mixture may be maintained in the temperature range of about 0° C. to about 90° C. for greater than about 5 minutes. After the addition of the aqueous solution of sodium ascorbate, the reaction mixture may be stirred for about 30 minutes at an elevated temperature. The aqueous solution of sodium ascorbate may be added at a rate that causes copper(I) 5-nitrotetrazolate to precipitate and/or at a rate that forms crystalline copper(I) 5-nitrotetrazolate. The method may further comprise washing the copper(I) 5-nitrotetrazolate at least one time.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

One aspect of the present subject matter is preparation of the compound copper(I) 5-nitrotetrazolate "DBX-1". Methods for preparing DBX-1 are contemplated in the present application. DBX-1 may be prepared by reacting copper(II) sulfate pentahydrate, sodium nitrite, 5-aminotetrazole and nitric acid and/or urea in water.

The components may be reacted under conditions suitable to synthesize DBX-1. Alternatively, the components may be reacted by mixing copper(II) sulfate pentahydrate and sodium nitrite in water and then adding a solution containing 5-aminotetrazole, nitric acid and copper(II) sulfate, also in water. The mixture may be maintained in the temperature range of about 0° C. to about 90° C., alternatively in the temperature range of about 0° C. to about 25° C., alternatively between 15-18° C., alternatively to about 16° C. The duration of the temperature control step may be a duration that is greater than about 5 minutes, alternatively greater than about 1 hour, alternatively, about 30 minutes. Nitric acid (or urea) may be added to the reaction and the mixture may be stirred for an additional period which may be greater than 5 minutes, alternatively greater than about 2 hours, alternatively, about 1 hour. The mixture may be heated to 100° C., alternatively greater than 90° C., and an aqueous solution of sodium ascorbate may be added at such a rate that DBX-1 begins to precipitate.

Once DBX-1 has begun to precipitate, sodium ascorbate may be added at such a rate as to form crystalline DBX-1. Once DBX-1 has formed, the reaction may be stirred for about 30 minutes at elevated temperature, alternatively it may be stirred for 5 minutes at elevated temperature. The DBX-1 precipitate may be isolated by filtration or by a suitable method known to those of skill in the art. The product may be washed either a single time or multiple times with water. Alternatively, the product may be washed a single time or multiple times with an alcohol, for example, isopropanol. Alternatively, the product may be washed with in multiple steps and in any order with both water and alcohol.

As an example, copper(II) sulfate pentahydrate and sodium nitrite may be dissolved in distilled water and a solution containing 5-aminotetrazole, nitric acid and copper(II) sulfate, also in distilled water, may be added dropwise. The reaction temperature during the addition may be maintained between 15-18° C. The mixture may then be stirred for 30 minutes followed by addition of nitric acid or urea (to decompose excess nitrite) and then stirring for an additional 1 hour. The solution may be heated to 100° C. and maintained at that temperature for 5 minutes at which time an aqueous sodium ascorbate solution may be added dropwise. The DBX-1 forms during addition of the sodium ascorbate and may be filtered off and washed with water to afford the product in >80% yield from 5-aminotetrazole.

It will be understood that DBX-1 may be prepared by reacting any suitable copper(II) salt or combination of copper (II) salts. Suitable copper(II) salts may include, but are not limited to, copper(II) sulfate or copper(II) nitrate. Likewise any suitable reducing agent or combination of reducing agents may be employed. Suitable reducing agents include, but are not limited to, sodium ascorbate. Likewise, any suitable solvent or combination of solvents may be used. Suitable solvents include, but are not limited to, water.

Regarding quantities of the components employed, sodium nitrite may be supplied in a molar ratio of about 2 moles to about 6 moles per mole of copper(II) sulfate pentahydrate. 5-Aminotetrazole may be supplied in a molar ratio of about 0.8 moles to about 1.2 moles per mole of copper(II) sulfate pentahydrate. Nitric acid may be supplied in a molar ratio of about 1 mole to about 6 moles per mole of copper(II) sulfate pentahydrate. For example, sodium nitrite may be supplied in a molar ratio of about 3 moles per mole of copper(II) sulfate pentahydrate, 5-aminotetrazole may be supplied in a molar ratio of about 1 mole per mole of copper(II) sulfate pentahydrate, while 2 moles of nitric acid may be supplied per mole of copper(II) sulfate pentahydrate. If used for decomposition of excess nitrite, urea may be supplied in a molar ratio of 0.5 moles per mole of excess nitrite added.

A solvent may be supplied in an amount that is suitable to effectuate the reaction between copper(II) sulfate pentahydrate, sodium nitrate, nitric acid and 5-aminotetrazole. As a more specific example, water (or other solvent) may be supplied in an amount that is suitable to effectuate the reaction between copper(II) sulfate pentahydrate, sodium nitrate, nitric acid and 5-aminotetrazole.

The reaction components may be combined in any order or sequence suitable to effectuate the reaction. By way of non-limiting example, the reaction of copper(II) sulfate pentahydrate, sodium nitrite, 5-aminotetrazole, nitric acid and sodium ascorbate may be carried out by adding a mixture of 5-aminotetrazole, nitric acid and copper(II) sulfate as an aqueous solution to an aqueous solution of copper(II) sulfate pentahydrate and sodium nitrite and adding nitric acid or urea followed by an aqueous solution of sodium ascorbate.

The products contemplated and made by the methods of the present application (in at least some aspects of the present subject matter, DBX-1) may be found suitable for use as explosives and, in particular, as an intermediate for primary explosives. Thus, the present application also contemplates methods for preparing compounds suitable for use as primary explosives, and explosive devices employing such compounds. Benefits include ease of preparation and low toxicity waste streams and health benefits for both military and commercial applications.

EXAMPLES

The following examples demonstrate the preparation and characterization of a material as taught herein.

Example 1

To a solution of 1.54 g (6.17 mmol) of copper(II) sulfate pentahydrate and 1.3 g (18.84 mmol) sodium nitrite in 20 mL distilled water was added dropwise a second solution composed of 0.53 g (6.23 mmol) 5-aminotetrazole, 0.75 mL 65% nitric acid, and 0.015 g of copper(II) sulfate pentahydrate in 15 mL distilled water. The temperature during addition was maintained at 15-18° C. After addition, the solution was stirred for 30 minutes followed by the addition of 1 mL 65% nitric acid and stirring for a further 1 hour. The solution was then heated to 100° C., maintained there for 5 minutes, followed by the addition of 10 mL of freshly-prepared 1M sodium ascorbate dropwise also at 100° C. Initially, the precipitated species re-dissolve during which time the addition can be at the rate of 2-3 drops per second. Once the DBX-1 precipitate begins to remain after addition, the dropping proceeds ideally when 5 drops are added at the rate of one per second, the solution is allowed to stir for 10 seconds, then 5 more drops are added. After addition is complete the solution is stirred for 5 minutes at 100° C., filtered while hot and rinsed with hot water. The filter cake is dried at 75° C. overnight. The yield is 0.98 g. (88%)

Example 2

To a solution of 1.43 g (6.17 mmol) of copper(II) nitrate and 1.3 g (18.84 mmol) sodium nitrite in 20 mL distilled water was added dropwise a second solution composed of 0.53 g (6.23 mmol) 5-aminotetrazole, 0.75 mL 65% nitric acid, and 0.013 g of copper(II) nitrate in 15 mL distilled water. The temperature during addition was maintained at 14-15° C. After addition the solution was stirred for 38 minutes followed by the addition of 0.19 g (6.38 mmol) urea and stirring for an additional 5 minutes. The solution was then heated to 100° C., maintained there for 5 minutes, followed by the addition of 10 mL of freshly-prepared 1M sodium ascorbate dropwise also at 100° C. Initially, the precipitated species re-dissolve during which time the addition can be at the rate of 2-3 drops per second. Once the DBX-1 precipitate begins to remain after addition, the dropping proceeds ideally when 5 drops are added at the rate of one per second, the solution is allowed to stir for 10 seconds, then 5 more drops are added. After addition is complete the solution is stirred for 5 minutes at 100° C., filtered while hot and rinsed with hot water. The filter cake is dried at 75° C. overnight.

Different arrangements of the components described above, as well as components and steps not described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above and various embodiments and modifications may be made without departing from the scope of the claims below.

That which is claimed is:

1. A method of preparing copper(I) 5-nitrotetrazolate comprising preparing an aqueous reaction mixture of copper(II) sulfate pentahydrate, sodium nitrite, 5-aminotetrazole, and at least one of nitric acid and urea.

2. The method of claim 1, further comprising maintaining the reaction mixture in the temperature range of about 0° C. to about 90° C. for greater than about 5 minutes.

3. The method of claim 1, further comprising adding an aqueous solution of sodium ascorbate to the reaction mixture.

4. The method of claim 3, further comprising stirring the reaction mixture for about 30 minutes at an elevated temperature.

5. The method of claim 3, wherein the aqueous solution of sodium ascorbate is added at a rate that causes copper(I) 5-nitrotetrazolate to precipitate.

6. The method of claim 3, wherein the aqueous solution of sodium ascorbate is added at a rate that forms crystalline copper(I) 5-nitrotetrazolate.

7. The method of claim 6, further comprising washing the copper(I) 5-nitrotetrazolate at least one time.

8. A method of preparing copper(I) 5-nitrotetrazolate, comprising the steps of:
(a) providing an aqueous solution of copper(II) sulfate pentahydrate and sodium nitrite;
(b) adding an aqueous solution of 5-aminotetrazole, nitric acid and copper(II) sulfate pentahydrate;
(c) combining said solutions to form a mixture while cooling the mixture;
(d) adding additional nitric acid to the mixture; and
(e) adding an aqueous solution of sodium ascorbate to the mixture.

9. The method of claim 8, further comprising
(f) maintaining the mixture in the temperature range of about 0° C. to about 90° C. for greater than about 5 minutes.

10. The method of claim 8, wherein the aqueous solution of sodium ascorbate has a 1M concentration.

11. The method of claim 10, further comprising
(g) stirring the mixture for about 30 minutes at an elevated temperature.

12. The method of claim 10, wherein the aqueous solution of sodium ascorbate is added at a rate that causes copper(I) 5-nitrotetrazolate to precipitate.

13. The method of claim 12, wherein the aqueous solution of sodium ascorbate is added at a rate that forms crystalline copper(I) 5-nitrotetrazolate.

14. The method of claim 13, further comprising
(h) washing the copper(I) 5-nitrotetrazolate at least one time.

15. A method for preparing copper(I) 5-nitrotetrazolate, comprising the steps of:
(a) providing an aqueous solution of copper(II) sulfate pentahydrate and sodium nitrite;
(b) adding an aqueous solution of 5-aminotetrazole, nitric acid and copper(II) sulfate pentahydrate;
(c) combining said solutions to form a mixture while cooling the mixture;
(d) adding urea to the mixture; and
(e) adding an aqueous solution of sodium ascorbate to the mixture.

16. The method of claim 15, further comprising
(f) maintaining the mixture in the temperature range of about 0° C. to about 90° C. for greater than about 5 minutes.

17. The method of claim 15, wherein the aqueous solution of sodium ascorbate has a 1M concentration.

18. The method of claim 15, wherein the aqueous solution of sodium ascorbate is added at a rate that causes copper(I) 5-nitrotetrazolate to precipitate.

19. The method of claim 18, wherein the aqueous solution of sodium ascorbate is added at a rate that forms crystalline copper(I) 5-nitrotetrazolate.

\* \* \* \* \*